(12) United States Patent  
Gribb et al.

(10) Patent No.: US 9,974,473 B2  
(45) Date of Patent: May 22, 2018

(54) SWALLOWING ASSESSMENT AND IMPROVEMENT SYSTEMS AND METHODS

(71) Applicant: Swallow Solutions, LLC, Madison, WI (US)

(72) Inventors: Tye Gribb, Madison, WI (US); JoAnne Robbins, Madison, WI (US); Jackie Hind, Madison, WI (US); John Peterman, Madison, WI (US)

(73) Assignee: SWALLOW SOLUTIONS, LLC, Madison, WI (US)

( * ) Notice: Subject to any disclaimer, the term of this patent is extended or adjusted under 35 U.S.C. 154(b) by 0 days. days.

(21) Appl. No.: 15/331,337

(22) Filed: Oct. 21, 2016

(65) Prior Publication Data

US 2017/0035345 A1    Feb. 9, 2017

Related U.S. Application Data

(63) Continuation of application No. 14/457,945, filed on Aug. 12, 2014, now Pat. No. 9,474,483.

(60) Provisional application No. 61/889,930, filed on Oct. 11, 2013, provisional application No. 61/877,712, filed on Sep. 13, 2013, provisional application No. 61/864,994, filed on Aug. 12, 2013.

(51) Int. Cl.  
*A61B 5/00* (2006.01)  
*A61B 5/08* (2006.01)

(52) U.S. Cl.  
CPC .......... *A61B 5/4205* (2013.01); *A61B 5/0002* (2013.01); *A61B 5/08* (2013.01); *A61B 5/4803* (2013.01); *A61B 5/682* (2013.01); *A61B 5/742* (2013.01); *A61B 2562/0247* (2013.01)

(58) Field of Classification Search  
CPC ... A61B 5/4205; A61B 5/4542; A61B 5/4557; A61B 2562/0247–2562/0252  
See application file for complete search history.

(56) References Cited

U.S. PATENT DOCUMENTS

| 4,334,542 | A | * | 6/1982 | Takinishi | ............... G09B 19/06 |
| | | | | | 434/185 |
| 4,629,424 | A | | 12/1986 | Lauks et al. | |
| 4,856,993 | A | * | 8/1989 | Maness | .................. A61C 19/05 |
| | | | | | 338/99 |
| 4,976,618 | A | | 12/1990 | Anderson | |
| 5,154,609 | A | | 10/1992 | George | |
| 5,954,673 | A | | 9/1999 | Staehlin | |
| 6,089,864 | A | | 7/2000 | Buckner et al. | |

(Continued)

FOREIGN PATENT DOCUMENTS

JP    2012112685 A    6/2012

OTHER PUBLICATIONS

Valbuza et al., "Swallowing dysfunction related to obstructive sleep apnea: a nasal fibroscopy pilot study." Sleep Breath. May 2011; 15(2):209-13.

(Continued)

*Primary Examiner* — Michael C Stout  
(74) *Attorney, Agent, or Firm* — Casimir Jones, S.C.; David Casimir

(57) ABSTRACT

The present disclosure relates to devices, systems, and methods for assessing and altering swallowing, speech, and breathing function. In particular, the present disclosure relates to devices and systems to assess and improve speech, breathing, and swallowing function in subjects in need thereof.

14 Claims, 6 Drawing Sheets

(56) References Cited

U.S. PATENT DOCUMENTS

| | | | |
|---|---|---|---|
| 6,210,339 B1 | 4/2001 | Klepen et al. | |
| 6,511,441 B1 | 1/2003 | Wakumoto et al. | |
| 6,702,765 B2 | 3/2004 | Robbins et al. | |
| 6,971,993 B2 | 12/2005 | Fletcher et al. | |
| 7,039,468 B2 | 5/2006 | Freed et al. | |
| 7,044,911 B2* | 5/2006 | Drinan | A61B 5/14539 600/300 |
| 7,238,145 B2 | 7/2007 | Robbins et al. | |
| 7,280,873 B2 | 10/2007 | Freed et al. | |
| 2003/0078521 A1* | 4/2003 | Robbins | A61B 5/228 600/587 |
| 2010/0036286 A1* | 2/2010 | Scholz | A61B 5/0002 600/590 |
| 2012/0123225 A1* | 5/2012 | Al-Tawil | G06F 3/011 600/301 |
| 2012/0179012 A1* | 7/2012 | Saffarian | A61B 5/0022 600/324 |
| 2012/0209089 A1* | 8/2012 | Garde | A61B 5/103 600/301 |
| 2012/0209148 A1* | 8/2012 | Barlow | A61B 5/038 600/590 |
| 2013/0211265 A1 | 8/2013 | Bedingham et al. | |
| 2013/0211849 A1* | 8/2013 | Essenpreis | G06F 19/3406 705/2 |
| 2014/0186793 A1 | 7/2014 | Kurti et al. | |
| 2014/0343373 A1* | 11/2014 | Shimoyama | A61B 5/03 600/301 |

OTHER PUBLICATIONS

Adams, et al., "A systematic review and meta-analysis of measurements of tongue and hand strength and endurance using the Iowa Oral Performance Instrument (IOPI)." Dysphagia. Sep. 2013;28(3):350-69.

European search report of related EP 14836503.4, dated Mar. 21, 2017, 8 pages.

* cited by examiner

SWALLOWING ASSESSMENT AND IMPROVEMENT SYSTEMS AND METHODS

The present application is a continuation of U.S. patent application Ser. No. 14/457,945, filed Aug. 12, 2014, which claims priority to U.S. Provisional Patent Application Ser. Nos. 61/864,994, filed Aug. 12, 2013, 61/877,712, filed Sep. 13, 2013, and 61/889,930, filed Oct. 11, 2013, the entire disclosures of which are herein incorporated by reference in their entireties.

FIELD OF THE INVENTION

The present disclosure relates to devices, systems, and methods for assessing and altering swallowing, speech, and breathing function. In particular, the present disclosure relates to devices and systems to assess and improve speech, breathing, and swallowing function in subjects in need thereof.

BACKGROUND OF THE INVENTION

Dysphagia, or swallowing disorder, is a general term used to describe the inability to move food from the mouth to the stomach. Some patients have limited awareness of their dysphagia, so lack of the symptom does not exclude an underlying disease or condition. When dysphagia goes undiagnosed or untreated, patients are at a high risk of pulmonary aspiration and subsequent aspiration pneumonia secondary to food or liquids going the wrong way into the lungs. Some people present with "silent aspiration" and do not cough or show outward signs of aspiration. Undiagnosed dysphagia also can result in dehydration, malnutrition, renal failure, and repeated episodes of aspiration pneumonia.

Swallowing disorders can occur in all age groups, resulting from congenital abnormalities, structural damage, and/or medical conditions. Swallowing problems are a common complaint among older individuals, and the incidence of dysphagia is higher in the elderly, in patients who have had strokes, and in patients who are admitted to acute care hospitals or chronic care facilities. Dysphagia is a symptom of many different causes, which can usually be identified through a careful history by the treating physician. A formal oropharyngeal dysphagia evaluation is performed by a speech language pathologist.

The goals of treatment are to maintain adequate nutritional and hydrational intake and to maximize airway protection. Rehabilitation therapy is the main stay of dysphagia management and allows for safe swallowing. Rehabilitation requires the cooperation of the patient and the ability of the patient to understand and follow commands. Typical therapy programs involve oral feeding with consistency modifications, compensatory strategies to reduce the risk of aspiration, strengthening therapy to increase muscle tone and augment oropharyngeal swallow, and medical therapies.

One condition related to dysphagia is obstructive sleep apnea. (See Valbuza et al., Swallowing dysfunction related to obstructive sleep apnea: a nasal fibroscopy pilot study, Sleep Breath 15(2):209-13 (2011)). Obstructive sleep apnea (OSA) is the most common category of sleep-disordered breathing. The muscle tone of the body ordinarily relaxes during sleep, and at the level of the throat the human airway is composed of collapsible walls of soft tissue which can obstruct breathing during sleep. Mild occasional sleep apnea, such as many people experience during an upper respiratory infection, may not be important, but chronic severe obstructive sleep apnea requires treatment to prevent low blood oxygen (hypoxemia), sleep deprivation, and other complications. Individuals with low muscle tone and soft tissue around the airway (e.g., because of obesity) and structural features that give rise to a narrowed airway are at high risk for obstructive sleep apnea. The elderly are more likely to have OSA than young people. Men are more likely to suffer sleep apnea than women and children.

Additional therapies are needed to assess and improve swallowing function, speech, and breathing functions.

SUMMARY OF THE INVENTION

The present disclosure relates to devices, systems, and methods for screening for and improving oropharyngeal strength generated for swallowing, speech, and breathing functions. In particular, the present disclosure relates to devices and systems to assess and improve swallowing, breathing, and speech functions in subjects in need thereof.

In some embodiments, provided herein are systems and methods comprising one or more or all of: an intraoral component comprising sensors that assess and/or improve swallowing capability; a communication component that transmits information from the sensors to an information processing component; an information processing component that collects, stores, and/or manages data received from the sensors; and a protocol component that manages and guides use of the system by clinician, the treated subject, and/or their caregiver.

In some embodiments, the intraoral component comprises: a flexible metal frame, one or a plurality of pressure sensors at one or more sensor locations on the frame, and/or a registration component proximal to the plurality of pressure sensors. In some embodiments, the frame is stainless steel. In some embodiments, the registration component comprises two sliding components configured to fit around the teeth (e.g., natural or artificial teeth), gum, or prosthesis of a subject. In some embodiments, the one or plurality of pressure sensors comprises one, two, three, four, five, or more sensors. In some embodiments, the frame is approximately 2 mm thick (e.g., 0.5 to 5 mm, 1 to 3 mm, etc.). In some embodiments, the frame is approximately 3 to 10 cm in length (e.g., 3, 4, 5, 6, 7, 8, 9, 10 cm or fractions thereof). In some embodiments, the frame is 0.1 to 1 cm in width (e.g., 0.2, 0.5, 0.75, etc.). In some embodiments, the frame has a composition and shape (e.g. thickness) that provides tensile strength, malleability, and ductability sufficient to withstand stress associated with repeated bending by a human hand up to 90 degrees (e.g., 10, 20, 30, 40, 50, 60, 70, 80, 90 degrees or fractions thereof).

In some embodiments, provided herein are methods of assessing swallowing function, comprising: a) contacting the aforementioned intraoral component with the mouth of a subject; and b) assessing swallowing function using the intraoral component. In some embodiments, the method further comprises the step of providing the subject a swallowing therapy program based on the swallowing function. In some embodiments, the contacting comprises bending the device to conform the device to the contours of the subject's hard palate. In some embodiments, the contacting comprises positioning the distal tip of a sensor at the boundary between the soft and hard palate. In some embodiments, the contacting comprises sliding one or more of the registration components around teeth or gums to secure the device in place.

In some embodiments, the intraoral component comprises a plurality of pressure sensors. In embodiments, the pressure sensors are located on a top surface of the frame that, when formed to a subject's mouth reside, make contact with the tissue of the hard palate (see e.g., FIG. 3 for upper mouth anatomy). In some embodiments, the pressure sensors are wireless, solid-state sensors. In some embodiments, the pressure sensors are actuated by pressure applied by the tongue to the lower surface of the frame.

In some embodiments, a communication component wirelessly communicates data collected by the sensors to the information processing component.

In some embodiments, the information processing component is a portable computing device, such as a tablet computer, comprising a processor. In some embodiments, the information processing component comprises a touchscreen display with a graphical user interface.

In some embodiments, the protocol component is contained on a computer readable medium that is implemented by the processor of the information processing component. In some embodiments, the protocol component comprises one or more or all of: a) a diagnostic protocol that displays, for example, a graphical diagnostic program to a subject, for assessing swallowing capability with the intraoral component and for recording and analyzing data collected from sensors from the implementation of the program; b) a therapeutic protocol that displays, for example, a graphical therapeutic program to a subject, for improving, maintaining, or preventing reduction in swallowing capability with the intraoral component and for recording and analyzing data collected from sensors from the implementation of the therapeutic program; and c) an alarm protocol that alerts subjects and/or their caregivers to actions or inactions that threaten optimized performance of the diagnostic or therapeutic protocols or to health changes that require medical intervention.

Further provided herein are methods for the system for assessing or improving swallowing capability.

In some embodiments, provided herein are methods and systems for chronic disease management comprising: a health monitoring device, a secure server, and a clinician device. In some embodiments, the health monitoring device is configured to send time-stamped metrics and collect, receive, manage, and/or store messages from the secure server; the secure server is configured to collect, receive, manage, and/or store time-stamped metrics from the health monitoring device and messages from the clinician device; the secure server is configured to send messages to the health monitoring device and alerts and/or reports to the clinician device; and the clinician device is configured to send messages to and collect, receive, manage, and/or store alerts and/or reports from the secure server.

In some embodiments, the health monitoring device collects, manages, and/or stores metrics regarding a subject's health and relays those metrics directly to the clinician device or indirectly to the clinician device via a secure server. In some embodiments, the metrics are transformed or modified by the secure server into alerts and/or reports. In some embodiments, a clinician analyzes the metrics, alerts, and/or reports and determines a treatment plan. In some embodiments, the clinician uses the clinician device to relay a treatment plan directly or indirectly via the secure server to the health monitoring device. In some embodiments, the health monitoring device implements the treatment plan by displaying messages to the subject, prompting the subject to perform various exercises, or modifying an existing treatment plan.

In some embodiments, provided herein are systems and methods for managing a subject's speech, breathing, and/or swallowing function, comprising software running on a computer that provides one or more or all of: a) one or more therapeutic protocols communicated over an electronic communication network and displayable on a patient computer; b) a clinician interface communicated over an electronic communication network and displayable on a clinician computer; and c) an administrative interface displayable on an administration computer. In some embodiments, the clinician interface and/or the administrative interface allows for the association of two or more health care facilities with a patient account or clinician account.

Additional embodiments are described herein.

DEFINITIONS

Figure 1:
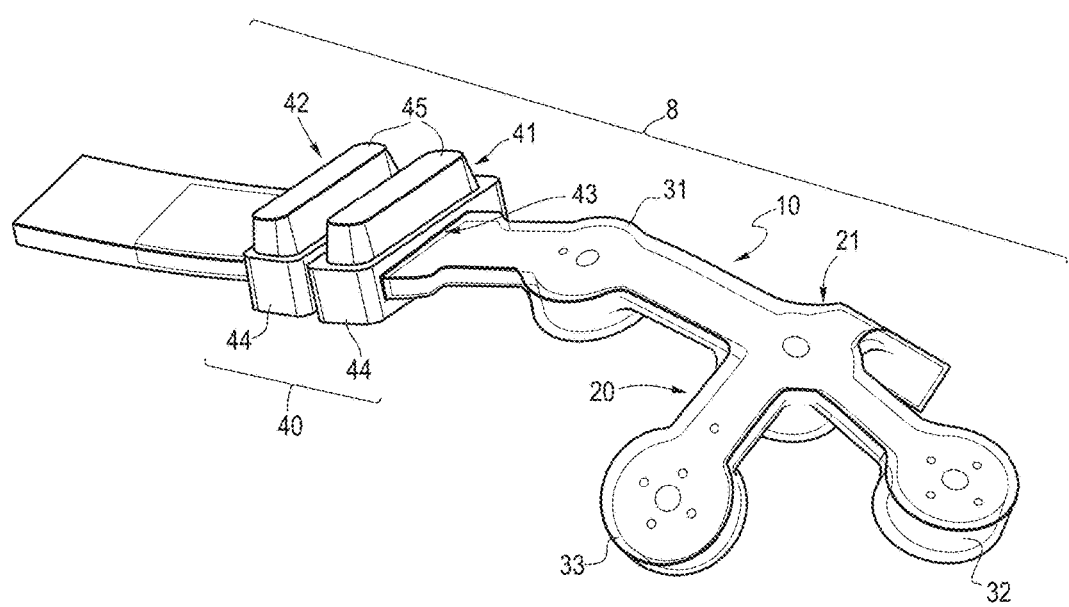
FIG. 1 shows an exemplary swallowing assessment device of embodiments of the present disclosure.

To facilitate understanding of the invention, a number of terms are defined below.

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "in electronic communication" refers to electrical devices (e.g., computers, processors, etc.) that are configured to communicate with one another through direct or indirect signaling.

DETAILED DESCRIPTION

The present disclosure relates to devices, systems, and methods for assessing and altering pressure necessary for adequate swallowing, speech, and breathing function. In particular, the present disclosure relates to devices and systems to assess and improve swallowing, breathing, and speech functions in subject in need thereof.

Approximately 40 mouth and throat pairs of muscles and many nerves are required for the complex, coordinated act of swallowing. The tongue propels food into the throat, which sends it on to the esophagus and stomach. During the transition from the mouth to the esophagus, the food or liquid moves past the larynx and trachea (windpipe), which lead directly to the lungs.

During swallowing, a trough is formed on the tongue by the intrinsic muscles. The trough obliterates against the hard palate from front to back, forcing the bolus to the back of the tongue. The intrinsic muscles of the tongue contract to make a trough (a longitudinal concave fold) at the back of the tongue. The tongue is then elevated to the roof of the mouth (by the mylohyoid (mylohyoid nerve), genioglossus, styloglossus and hyoglossus) such that the tongue slopes downwards posteriorly. The contraction of the genioglossus and styloglossus also contribute to the formation of the central trough.

At the end of the oral preparatory phase, the food or liquid bolus has been formed and is ready to be propelled posteriorly into the pharynx. In order for anterior to posterior transit of the bolus to occur, orbicularis oris contracts and adducts the lips to form a tight seal of the oral cavity. Next, the superior longitudinal muscle elevates the apex of the tongue to make contact with the hard palate and the bolus is propelled to the posterior portion of the oral cavity. Once the bolus reaches the palatoglossal arch of the oropharynx, the pharyngeal phase, which a patterned response, then begins. Receptors initiating this response are proprioceptive. They are scattered over the base of the tongue, the palatoglossal and palatopharyngeal arches, the tonsillar fossa, uvula and posterior pharyngeal wall. Stimuli from the receptors of this phase then provoke the pharyngeal phase.

For the pharyngeal phase to work properly all other egress from the pharynx must be occluded—this includes the nasopharynx and the larynx. When the pharyngeal phase begins, other activities such as chewing, breathing, coughing and vomiting are concomitantly inhibited.

The soft palate is tensed by tensor palatini (Vc), and then elevated by levator palatini (pharyngeal plexu) to close the nasopharynx. There is also the simultaneous approximation of the walls of the pharynx to the posterior free border of the soft palate, which is carried out by the palatopharyngeus (pharyngeal plexus) and the upper part of the superior constrictor (pharyngeal plexus).

The pharynx is pulled upward and forward by the suprahyoid and longitudinal pharyngeal muscles—stylopharyngeus, salpingopharyngeus (pharyngeal plexus) and palatopharyngeus (pharyngeal plexus) to receive the bolus. The palatopharyngeal folds on each side of the pharynx are brought close together through the superior constrictor muscles, so that only a small bolus can pass.

The actions of the levator palatini (pharyngeal plexus) tensor palatini and salpingopharyngeus (pharyngeal plexus) in the closure of the nasopharynx and elevation of the pharynx opens the auditory tube, which equalizes the pressure between the nasopharynx and the middle ear. This does not contribute to swallowing, but happens as a consequence of it.

The oropharynx is kept closed by palatoglossus (pharyngeal plexus), the intrinsic muscles of tongue and styloglossus.

It is true vocal fold closure that is the primary laryngopharyngeal protective mechanism to prevent aspiration during swallowing. The adduction of the vocal cords is effected by the contraction of the lateral cricoarytenoids and the oblique and transverse arytenoids (all recurrent laryngeal nerve of vagus). Since the true vocal folds adduct during the swallow, a finite period of apnea (swallowing apnea) must necessarily take place with each swallow. When relating swallowing to respiration, it has been demonstrated that swallowing occurs most often during expiration, even at full expiration a fine air jet is expired probably to clear the upper larynx from food remnants or liquid. The clinical significance of this finding is that patients with a baseline of compromised lung function will, over a period of time, develop respiratory distress as a meal or oral hydrational intake progresses. Subsequently, false vocal fold adduction, adduction of the aryepiglottic folds and retroversion of the epiglottis take place. The aryepiglotticus (recurrent laryngeal nerve of vagus) contracts, causing the arytenoids to appose each other (closes the laryngeal aditus by bringing the aryepiglottic folds together), and draws the epiglottis down to bring its lower half into contact with arytenoids, thus closing the aditus. Retroversion of the epiglottis, while not the primary mechanism of protecting the airway from laryngeal penetration and aspiration, acts to anatomically direct the food bolus laterally towards the pyriform fossa. Additionally, the larynx is pulled up with the pharynx under the tongue by stylopharyngeus, salpingopharyngeus (pharyngeal plexus), palatopharyngeus (pharyngeal plexus) and inferior constrictor (pharyngeal plexus). This phase is passively controlled relatively automatically and involves cranial nerves.

The hyoid is elevated by digastric and stylohyoid, lifting the pharynx and larynx up even further. The bolus moves down towards the esophagus by pharyngeal peristalsis which takes place by sequential contraction of the superior, middle and inferior pharyngeal constrictor muscles (pharyngeal plexus). This muscular sequence also cleans up residue in the pharynx after the swallow. The lower part of the inferior constrictor (cricopharyngeus) is normally closed and only opens for the advancing bolus.

The esophageal phase of swallowing is under involuntary neuromuscular control. Propagation of the food bolus is significantly slower than in the pharynx. Finally the larynx and pharynx move down with the hyoid mostly by elastic recoil.

Obstructive sleep apnea (OSA) is the most common category of sleep-disordered breathing. The muscle tone of the body ordinarily relaxes during sleep, and at the level of the throat the human airway is composed of collapsible walls of soft tissue which can obstruct breathing during sleep. Mild occasional sleep apnea, such as many people experience during an upper respiratory infection, may not be important, but chronic severe obstructive sleep apnea requires treatment to prevent low blood oxygen (hypoxemia), sleep deprivation, and other complications. Individuals with low muscle tone and soft tissue around the airway (e.g., because of obesity) and structural features that give rise to a narrowed airway are at high risk for obstructive sleep apnea. The elderly are more likely to have OSA than young people. Men are more likely to suffer sleep apnea than women and children.

Loss of swallowing, speech, or breathing capability, which may be caused by any number of factors, creates multiple health risks, as described in the background section above. The systems and methods herein allow subject and their caregivers to assess swallowing, speech, or breathing capability and to improve swallowing, speech, or breathing capability, if needed.

In some embodiments, the system comprises one or more or all of: an intraoral component, a communication component, an information processing component, and a protocol component. Illustrative embodiments of each of these components, and their integration into the system, is described below. In some embodiments, systems and methods of chronic disease management are provided comprising a patient device, a secure server, and a clinician device as described below.

I) Intraoral Component

In some embodiments, the systems and methods comprise an intraoral component. The intraoral component can provide a variety of functions, including but not limited to: the ability to assess swallowing capability or a sub-component of swallowing (e.g., muscle strength of particular muscles or regions of muscles), qualitatively and/or quantitatively; the ability to monitor swallowing at particular time intervals or in real-time; and the ability to improve, maintain, or reduce the reduction in swallowing capability using a therapeutic protocol.

Exemplary subcomponents of the intraoral component include, but are not limited to: a frame configured for placement of the intraoral component in the mouth of a subject; one or more sensor locations positioned on the frame; one or more sensors positioned at the sensor locations; a computer chip with a serial number; and a registration component that positions the intraoral component relative to a physical architecture of the subject (e.g., teeth, gum, artificial prosthesis, etc.).

In some embodiments, the frame is shaped for desired placement in a mouth of the subject (e.g., a human subject). In some embodiments, the placement is on the roof of the mouth, whereby the intraoral device makes physical contact with the roof of the mouth. In some embodiments, the intraoral device makes physical contact with the roof of the mouth over a substantial portion of the surface area of the frame (e.g., over 50% of one surface of the frame makes contact with the roof of the mouth, over 60%, 70%, 80%, 90, 95%, . . . , 100%). The intraoral component is not limited by the shape of the frame. Any number of frame shapes may be employed. In some embodiments, the frame comprises a central linear portion having a distal end that is positioned towards the back of the mouth and a proximal end that is positioned towards the anterior opening of the mouth. In some embodiments, the central linear portion is rectangular in its length/width dimensions and is relatively thin (e.g., less than 5 mm, less than 3 mm, less than 2 mm, less than 1 mm) in its depth dimension. In some embodiments, one or more branches (e.g., linear branches) extend outward from the central linear portion. For example, in the embodiment shown in FIG. 2, a linear central portion 10 of the frame 5 of the intraoral component comprises first 20 and second 21 linear branches extending outward at a 90% angle. The frame may have fewer (e.g., zero, one) or greater (e.g., 3, 4, 5, 6, etc.) numbers of branches in any desired orientation, shape, or position.

In some embodiments, the frame is formed to fit within the roof of the mouth. In some such embodiments, the frame may be configured for an average subject (e.g., "one size fits all") or may be provided in several different one size fits all categories (e.g., small, medium, large, child, etc.). In other embodiments, a frame may be designed (e.g., based on a cast mold) for a patient-specific fit. In yet other embodiments, the frame may be bendable or otherwise configurable to adjust to fit the mouth a specific subject. An exemplary fitted intraoral component 8 is shown in FIG. 1. The device has a curved central linear portion 10. Two curved linear branches, 20 and 21, are provided.

Outside of physical constraints of the mouth, comfort considerations, and utility considerations, the intraoral device is not limited in the dimensions of the frame. However, in some embodiments, particularly those where the frame is adjustable, dimensions are selected to permit easy adjustment by a caregiver or by a subject while also providing sufficient durability to withstand adjustment (e.g., multiple adjustments). Such dimensions may be weighed also in view of the materials selected (described in more detail below). Referring back to the embodiments shown in FIG. 2, in some embodiments, the central linear portion is approximately 2 mm thick (e.g., 0.5 to 5 mm, 1 to 3 mm, etc.). In some embodiments, central linear portion is approximately 3 to 10 cm in length (e.g., 3, 4, 5, 6, 7, 8, 9, 10 cm or fractions thereof). In some embodiments, the central linear portion is 0.1 to 1 cm in width (e.g., 0.2, 0.5, 0.75, etc.). The linear branches may be similarly dimensioned or may be longer, shorter, thinner, or wider, as desired. Typically, the linear branches are shorter and narrower than the central linear portion. The width and thickness need not be constant through the length of the central linear portion or the linear branches.

Figure 2:
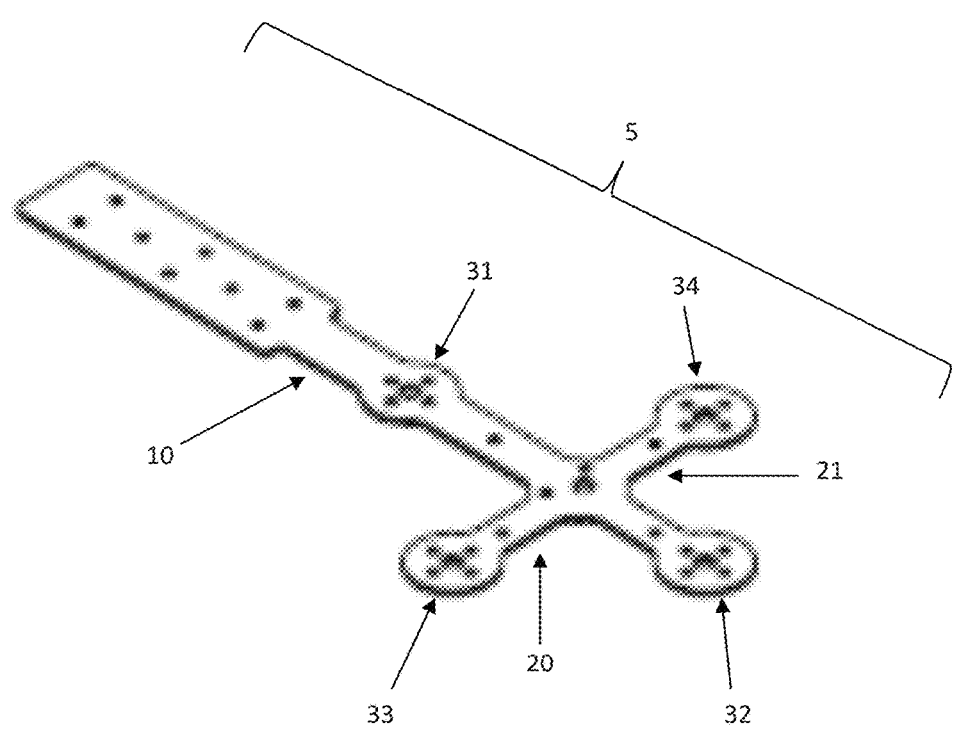
FIG. 2 shows a drawing of a metal spline of an exemplary swallowing assessment device of embodiments of the present disclosure.
Figure 3:
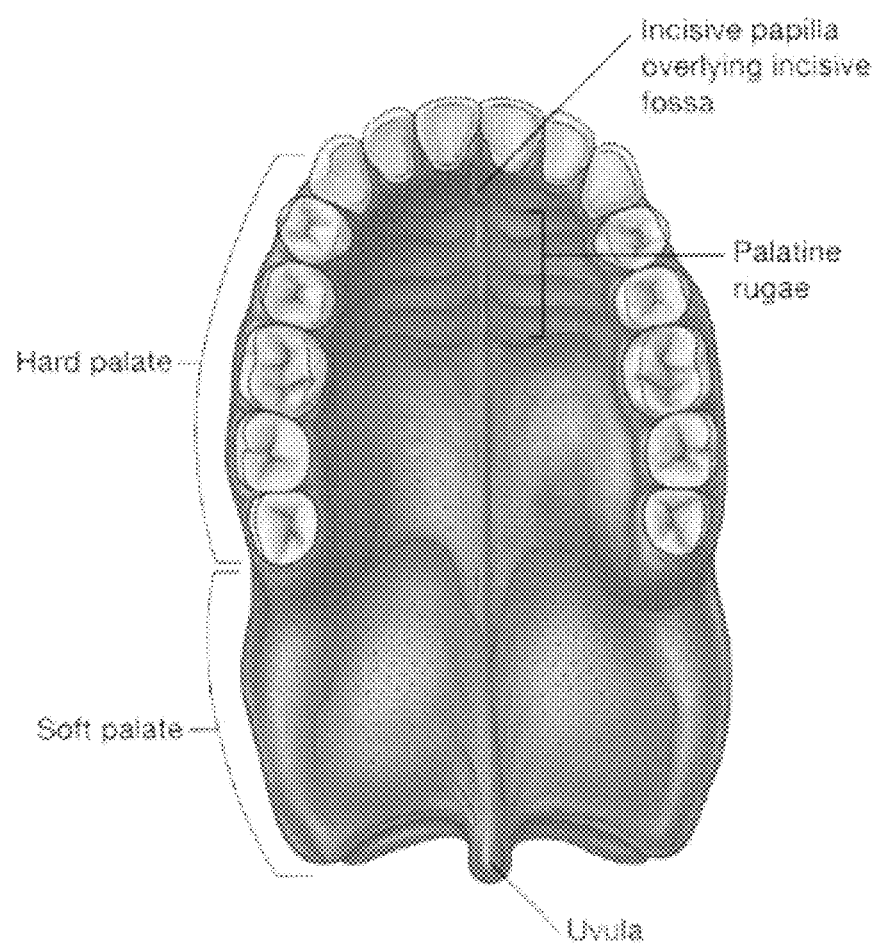
FIG. 3 shows a diagram of a human hard and soft palate.
Figure 4:
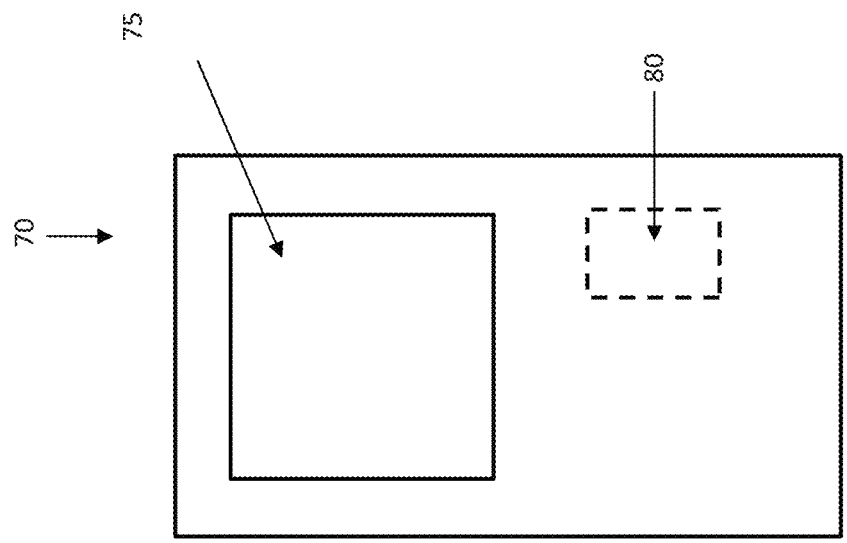
FIG. 4 shows an embodiment of a system comprising an intraoral component 8 comprising a plurality of pressure sensors 50, a communication component 60 (e.g., wireless transmitter), an information processing component 70 comprising a display 75, and a protocol component 80 (e.g., embodied in a computer memory within the information processing component).
Figure 4:
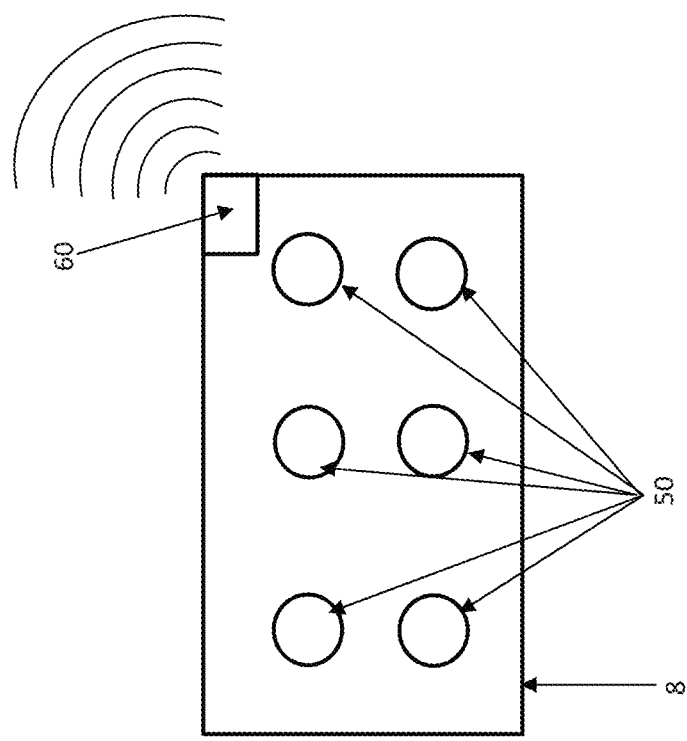

The frame may be made of any suitable material, including but not limited to, metals, ceramics, and plastics, or combinations thereof. Preferably the frame is made of a biocompatible material or is coated with or encompassed within a biocompatible material. In some embodiments, the frame uses a material and shape (e.g. thickness) that provides tensile strength, malleability, and ductability sufficient to withstand stress associated with repeated (e.g., 2×, 3×, 5×, 10×, 100×, 1000×, 10,000×, etc.) bending by a human hand up to 90 degrees (e.g., 10, 20, 30, 40, 50, 60, 70, 80, 90 degrees or fractions thereof). In some embodiments, the frame is made of stainless steel (e.g., stainless steel type 316). Embodiments constructed of stainless steels and dimensioned as shown in FIG. 2 have demonstrated durability and adjustability for optimized fit with a human subject's mouth.

In some embodiments, the frame comprises attachment features (e.g., holes, pins, latches, tabs, snaps, ridges, etc.) that permit other components to be attached to the frame (e.g., sensors, coatings, coverings, communication components, etc.). In some embodiments, the frame comprises markings or other fiducials for monitoring, visually or electronically, the position of the frame while the device is being manufactured, placed into an oral cavity of a subject, or used.

In some embodiments, the intraoral component comprises one or more sensor locations: i.e., locations on the frame or attached to the frame and configured for the placement of a sensor. In some embodiments, the sensor locations comprise regions of the frame that are shaped for the mounting of a sensor. For example, as shown in FIG. 2, four circular regions 30 are provided on the frame as sensor locations: a first sensor location 31 centrally located along the central portion 10 of the frame, a second sensor location 32 located at the distal end of the central portion 10 of the frame, a third sensor location 33 located at the distal end of branch 20, and a fourth sensor location 34 located at the distal end of branch 21. The intraoral device may have any number of desired sensor locations (e.g., 1, 2, 3, 4, 5, 6, 7, 8, 9, 10, etc.). Further, the sensor locations may be positioned at any desired location on the frame. In some embodiments, the sensors are of appropriate number and location to facilitate the use of the device (e.g., qualitative or quantitative assessment of swallowing; maintenance or improvement of swallowing; etc.). For example, in some embodiments, the sensor location 32, located at the distal-most point of the frame is positioned to reside at the back boundary of the hard palate of a subject. The sensor locations may have any desired size and shape. In some embodiments, the size and shape of the sensor location is selected to provide an appropriate base of attachment for a sensor: stability, reliability, physical placement relative to the architecture of the subject's oral cavity, shape/size of the sensor, accommodating any communication components (e.g., wires) associated with a sensor, etc. In some embodiments, the sensor locations comprise attachment features (e.g., holes, pins, latches, tabs, snaps, ridges, etc.) for associating a sensor with the sensor location. In some embodiments, the sensor locations comprise markings or other fiducials for monitoring, visually or electronically, the position of the sensor locations while the device is being manufactured, placed into an oral cavity of a subject, or used.

In some embodiments, the intraoral component comprises one or more sensors (e.g., positioned at one or more of the sensor locations). In some embodiments, the sensors are positioned on the lower surface of the frame when the upper surface of the frame is in contact with the hard palate of the oral cavity of a subject. In other embodiments, the sensors are positioned on the upper surface, such that they reside between the frame and the tissue of the hard palate of the oral cavity of a subject. In some embodiments, the sensors are on both the upper and lower side of the frame at one or more sensor locations. In some such embodiments, a single sensor may extend around the edge of the frame and occupy both sides of the frame at the sensor location. In other embodiments, a first sensor is located on one side of a sensor location and a second sensor is located on the other side of the sensor location.

Sensors may be employed that sense any desired property. In some embodiments, the sensors detect force or pressure changes. For example, in some embodiments, the sensors detect force or pressure applied by the tongue directly to a sensor or applied by the tongue to the frame, applying force or pressure on a sensor located between the frame and tissue. In some embodiments, sensors are used that detect one or more of: motion, magnetic field, gravity, humidity, moisture, vibration, electrical field, position (e.g., of the tongue), temperature, chemicals or molecules (e.g., ethanol, toxins, nutrients, pheromones, oxygen, carbon dioxide, glucose, hormones, cytokines), organisms (e.g., pathogens), light, sound, and pH. Such sensors include, but are not limited to, geophones, hydrophones, lace sensors, microphones, seismometers, chemical sensors, electrochemical gas sensors, ion-selective electrodes, infrared point sensors, nondispersive infrared sensors, redox electrodes, olfactometers, current sesnors, galvanometers, magnetometers, MEMS magnetic field sensors, voltage detectors, air flow meters, flow sensors, accelerometers, gyroscopes, capacitive displacement sensors, gravimeters, inclinometers, laser rangefinders, laser surface velocimeters, tilt sensor, photodetectors, barographs, barometers, bourdon gauges, piezometers, pressure sensors (e.g., absolute pressure sensors, gauge pressure sensors, differential pressure sensors, sealed pressure sensors), tactile sensors, time pressure gauges, force gauge, viscometer, thermometer, motion detector, occupancy sensor, proximity sensor, and triangulation sensor. Pressure sensors include, but are not limited to, force collector types (e.g., piezoresistive strain gauges (e.g., silicon (monocrystalline), polysilicon thin film, bonded metal foil, thick film, and sputtered thin film); capacitive (e.g., metal, ceramic, and silicon diaphragms); electromagnetic (e.g., measurement of displacement of a diaphragm by means changes in inductance, LVDT, Hall Effect, or by eddy current principle); piezoelectric, optical (e.g., using fiber bragg gratings); and potentiometic) and other types (e.g., resonant; thermal; and ionization).

In some embodiments, sensors operate in continuous mode, for example collecting data in real-time or at desired time points. In other embodiments, sensors operate on command at designated time points or time intervals. Sensors may receive information (e.g., operating instructions) or transmit information (e.g., collected data) via any desired communication mechanism, including wired and wireless approaches.

In some embodiments, for pressure sensors to detect pressure applied by the tongue, the size and shape of the sensors is selected to accommodate location of the sensor itself or the sensor location on the frame by the tongue of a subject and to permit pressing of the tongue on the intraoral device to actuate the sensor.

In some embodiments that employ a pressure sensor, the pressure sensor detects the amount of pressure applied to the sensor. Pressure amounts may be measured in any desirable units (e.g., pounds per square inch (psi), pounds per square foot (psf), kilograms-force per square centimeter ($kgf/cm^2$), kilopound per square inch (ksi), Pascals (Pa), Torrs, bars (bar), baryes (Ba), atmospheres (at), arbitrary units, etc.) and may be strictly quantitative or semi-quantitative (e.g., pressure ranges assigned as a single value; e.g., high, medium, low, etc.). In some embodiments, the pressure sensor detects the timing of pressure applied to sensor. In some embodiments, the pressure sensor detects a change in pressure over time applied to the sensor. In some embodiments, the pressure sensor detects one or more threshold pressure events (e.g., the existence of a defined pressure amount at a point in time).

In some embodiments each sensor present on the intraoral device, if multiple are present, act independently of one another. In other embodiments, two or more sensors work in a coordinated fashion. For example, in some embodiments, pressure is applied to two or more sensor simultaneously and, alternatively, a pressure value at each sensor is measured or a summed pressure at plurality of sensors is measured. In some embodiments, two or more sensors are located in immediate proximity to one another and each member of the set measure pressure at a different time point during a pressure event.

Wires, if used, may be directed from the sensor(s) along the length of the frame, for example, terminating at the proximal end of the frame.

In some embodiments, INTERLINK ELECTRONICS FSR sensors (FORCE SENSING RESISTOR) are employed. FSRs are robust polymer thick film (PTF) devices that exhibit a decrease in resistance with increase in force applied to the surface of the sensor. Such sensors actuate force as low as 0.2N, are low cost, ultra-thin, robust (up to 10 million actuations), and simple and easy to integrate into the intraoral component. Other similar sensors may also be employed. In some embodiments, such ultra-thin sensors comprise a bottom substrate, a gusset layered on the bottom substrate outside of the active area, the sensor electronics adjacent to the gusset and forming the active area, and, optionally, a spacer adhesive adjacent to the sensor electronics opposite the gusset. A top substrate is layered over the sensor electronics and the spacer adhesive and an adhesive layer is layered on top of the top substrate.

In some embodiments, the gusset provides a distinct region which the subject can feel with his or her tongue in order to accurately direct lingual pressure to the pressure sensor. In some embodiments, the gusset is made of foam (e.g., silicone foam).

In some embodiments, sensors are prepared or placed by printing technologies. For example, in some embodiments, one or more sensors is printed on a solid support under computer control to provide exact location and size and consistent design from device to device.

In some embodiments, the intraoral component comprises a power source that powers any electrical components. In some embodiments, the power source is one or more batteries.

In some embodiments, the intraoral component comprises a registration component. The registration component functions to fix the location of the intraoral component in an oral cavity of a subject relative to physical architecture—typically a portion of the subject's body. In some embodiments, the physical architecture is the subject's teeth (e.g., natural or artificial) or gums. In some embodiments, the architecture is a prosthesis or appliance (e.g., denture, Ajers' clasp, veneer, removable partial denture (RPD), braces, retainer, palatal expander, bite plate, headgear, facemask, forsus/herbst, pendex/pendulum, lip bumper, space maintainer, spacer/separator, etc.).

In some embodiments, the intraoral component comprises a computer chip with a serial number. The computer chip functions to uniquely identify the intraoral device. In some embodiments, information generated by the intraoral device (e.g., time-stamped metrics) includes the unique serial number of the intraoral device. Identification of the particular device responsible for generating a given piece of information allows a clinician to maintain accurate records and make appropriate treatment decisions.

FIG. 1 shows an exemplary embodiment of a registration component configured for positioning an intraoral component relative to the teeth or gums of a subject (or denture, etc.). In some embodiments, the registration component comprises one or more sub-components. In some embodiments, one of the plurality of components is movable (e.g., able to slide along a portion of the intraoral component frame) and the other registration components are immobile (e.g., affixed to the intraoral component frame). In some embodiments, the device comprises two registration components that both are movable (e.g., able to slide alone a portion of the intraoral component frame). In some embodiments, a moveable component is moved to the appropriate position and locked into place. In some embodiments, locking is achieved by a locking mechanism, including but not limit to, a latch, a hook and eye, peg and hole, suction, physical attachment to the architecture, or any other desired mechanism. In some embodiments, the moveable sub-component of the registration component is restrained by friction, such that a first force is needed to move the sub-component (e.g., a force applied from a subject hand or a treating physician's hand), but a second force (e.g., forces generated during the normal use of the intraoral component) is insufficient to move the sub-component. Such friction can be generated by choice of materials (e.g., rubber, plastic, or other materials having a sufficient coefficient of friction relative to the surface on which they move) and/or sizing of the sub-components (e.g., providing a snug fit around the frame of the intraoral component).

In some embodiments, the placement of the intraoral component location is adjusted using the registration component. In other embodiments, the intraoral component is first positioned into the oral cavity and then the registration component is used to lock the intraoral component into that position.

In the example shown in FIG. 1, two sub-components 41 and 42 of a registration component 40 are shown. Each of the sub-components comprises an interior opening 43 through which the central portion of the frame 10 of the intraoral device is inserted. As shown in FIG. 1, the interior opening 43 is sized to provide a tight fit around the frame. Each sub-component has a base 44 and an upper region 45 having a smaller surface area than the base on which is sits. As such, when the two sub-components 41 and 42 are positioned in proximity to one another along the central portion of the frame 10, a gap is created between the respective upper regions of the two sub-components. In some embodiments, the teeth of a subject are positioned within the space between the bases of the two sub-components in physical contact with the interior surface of one or both bases and the gums fit between the gap created between the respective upper regions.

One or more of the sub-components of the intraoral component may be coated or covered, for example, with rubber, plastic, or other desired materials (e.g., silicone such as MASTERSIL 151MED, Qmed). Coatings may be used for any number of reasons, including but not limited to, providing a biocompatible contact surface, sealing electronic components from fluid, moisture, or other materials of the oral cavity of a subject, holding in place sensors, wires, or other sub-components to the frame, providing a frictional surface for a movable registration component, providing pleasant mouth feel and taste, increasing durability, and providing an easy to handle surface texture for placement in the oral cavity and use.

In some embodiments, the intraoral component is configured as a disposable, single-use or limited use device. As such, after one use or after multiple separate uses by a subject for a set period of time (e.g., 1 day, 1 week, 1 month with, for example, daily use) the intraoral component is disposed of and if continued use is needed, a new intraoral component is provided. In some embodiments, for disposable use, the intraoral component is packaged separately from other components of the system. Packing may include two or more intraoral components. Preferably, each intraoral component is independently packaged (e.g., in a sealed sterile container, such as a plastic bag), even if two or more such intraoral components are sold or provided together (e.g., in a box). In some embodiments, the packaging provides written or diagrammatic indicia conveying information about the specific intraoral component, including, for example, the name or other identifier of a specific subject for whom the intraoral component is intended.

In some embodiments, the intraoral component comprises a tracker that tracks the amount of time the intraoral component has been used and/or tracks the number of times one or more sensors has been activated. In some such embodiments, once a maximum recommended use level has been achieved, an alarm or warning is provided indicating that the intraoral component use should be discontinued and a new intraoral component used in its place.

While exemplary intraoral components have been described above, it should be understood that various embodiments of the systems and methods provided herein may employ different intraoral component designs and configurations. For example, the intraoral devices described in U.S. Pat. No. 7,238,145 and U.S. Pat. Publ. No. 2003/0078521, each of which is herein incorporated by reference in its entirety, may be employed. In some embodiments, the intraoral component employs an IOPI device (IOPI Medical, Redmond, Wash.) (see e.g., Adams et al., Dysphagia, 2013, Mar. 7 Epub), herein incorporated by reference in its entirety). In some embodiments, the intraoral component employs an electrical neuromuscular stimulator (see e.g., U.S. Pat. Nos. 7,039,468 and 7,280,873, herein incorporated by reference in their entireties).

II) Communication Component

In some embodiments, the systems and methods comprise a communication component. In some embodiments, the communication component communicates information from the sensors to an information processing component. In some embodiments, the communication component communicates information to the sensors (e.g., from the information processing component). In some embodiments, the communication component communicates information from any one component of the system (e.g., a tracking component on the intraoral component) to any other component of the system or between two sub-components of the system.

In some embodiments, a portion or all of the communication component is wired. For example, in some embodiments, the communication component comprises wires connecting the sensors directly or indirectly to an information processing component (e.g., computer). In some embodiments, each sensor is attached by one or more wires directly or indirectly to an information processing component. FIG. 1 shows one embodiment of such a wired connection. In FIG. 1, each sensor is connected at each sensor location to a metal wire. The wire travels from the sensor either along the linear branch or the central linear portion of the frame of the intraoral component. The wires run together in parallel to the proximal end of the central linear portion of the frame of the intraoral component. In this embodiment, the wires are contained within a channel in a rubber coating of the intraoral component. In some embodiments, the wires travel from the proximal end of the intraoral device to a signal processing component that converts analog information from the sensor into digital information. In some embodiments, the wires terminate at an adaptor at the proximal end of the intraoral device. In such embodiments, a cable may be employed to transfer the signal from the wires to a signal processing component by plugging the cable into the adapter. In some embodiments, the signal processing component is attached to the information processing component via a cable.

In some embodiments, a portion of or the entire communication component is wireless. Any desired wireless communication technology may be employed, including but not limited to, electromagnetic wireless telecommunications (e.g., two-way radio, wireless networking, cellular, satellite), light (e.g., visible, infrared (IR), etc.), sonic (e.g., ultrasonic), electromagnetic induction, etc. Where wireless sensor networks are employed, any desired protocol can be used (e.g., ZigBee, EnOcean, Personal area networks, Bluetooth, TransferJet, Ultra-wideband).

In some embodiments, the intraoral component comprises a wireless communication component such that signal generated from the sensor(s) is transmitted to an information processing component wirelessly. In some such embodiments, the intraoral component does not contain communication wires. In some such embodiments, no signal processing component is needed or used to convert analog information into digital information prior to receipt of information by the information processing component. In some embodiments, the communication component communicates information (e.g., time-stamped metrics) comprising sensor data and/or a unique serial number associated with the device via a chip to an information processing component.

III) Information Processing Component

In some embodiments, the systems and methods comprise an information processing component. The information processing component can provide a variety of functions, including but not limited to: receiving and processing information generated by the sensors; receiving and processing information generated by chip with a serial number; displaying information to a subject; displaying information to a caregiver; storing information; storing, transmitting, executing, and/or displaying protocols (e.g., diagnostic or therapeutic protocols); tracking use of the intraoral component; and presenting alarms.

In some embodiments, the information processing component comprises one or more of a computer processor, computer readable medium, and software. Any of a variety of computing devices may be used as the information processing component, including but not limited to, a desktop computer, a mainframe computer, a laptop computer, a personal digital assistant (PDA), a portable computer (e.g., mobile devices such as telephones), a tablet computer (e.g., standard tablets, slates, mini tablets, phablets, customer handheld devices), and a wearable computer (e.g., helmet, eyeglass, wristwatch, clothing, etc.).

In some embodiments, the information processing component or a device in electronic communication with the information processing component (e.g., a video monitor) comprises a display. In some embodiments, the display displays textual and/or graphical information to a user (e.g., a subject using an intraoral component). In some embodiments, the display displays information to the user related to pressure readings in real-time. In some embodiments, the display is a touchscreen display, permitting the user to select and manage system functions via a graphical interface. In some embodiments, audio information is conveyed (e.g., via speakers, headphones, etc.). In some embodiments, a graphical image is presented to the user in the form of a meter with a bar indicating the current pressure applied. In some embodiments, the meter includes color zones that signify goal regions (e.g., one color too low; one color in target region; one color over goal). In some embodiments, the meter further comprises a numerical read-out showing a quantitative amount of pressure applied (e.g., in hPa units). In some embodiments, the interface further provides textual instructions (e.g., keep pressing; press harder; goal met). In some embodiments, the interface provides an additional graphical interface of goals met (e.g., thumbs up/thumbs down). In some embodiments, the interface shows an image of the intraoral device and sensors, indicating which sensor is active or to be targeted. The user interface may also provide step by step instructions of setting up, using, and managing the devices and systems. The interface may launch automatically when an intraoral device is plugged into a user's computing device.

In some embodiments, the information processing component or a device in electronic communication with the information process component comprises a networking component. The networking component receives and/or transmits information to the communication component.

In some embodiments, the computer readable medium comprises a database containing protocols, subject data, historic data, or other desired information.

In some embodiments, the information processing component comprises an artificial intelligence component (e.g., embodied in software running on the processor). In some embodiments, the artificial intelligence component alters stored protocols in response to data obtained from one or more subjects.

IV) Protocol Component

In some embodiments, the systems and methods comprise a protocol component. The protocol component comprises instructions, typically embodied in software, for managing the diagnostic and therapeutic use of the systems and methods. In some embodiments, the protocol component is stored in a computer readable medium. In some embodiments, the protocol component is embodied in the information processing component.

In some embodiments, the protocol component directs the display of information. In some embodiments, the display comprises instructions (e.g., graphical, textual, audio, etc.) for use of the intraoral component. For example, in some embodiments, a graphical image of the intraoral device is provided on the display showing the location and timing of sensors to be actuated by the user. In some embodiments, a graphical cue, such as a color change or motion is used to indicate which sensor to actuate. In some embodiments, quantitative information is conveyed. For example, the amount of pressure applied to a sensor is shown either numerically or graphically (e.g., degree of color change, size of graphical indicator, etc.). In some embodiments, information conveyed comprises knowledge of performance completing a task (e.g., "goal met or not met"). In some embodiments, the format of the display is adjustable to accommodate any subject type, including those with impaired vision or hearing, impaired cognitive skills, color blindness, young age, varied language skills or knowledge, etc.

In some embodiments, the protocol component comprises data storage and management capabilities. Data storage includes data storage and management for individual subjects, for example, to monitor swallowing capability over time. In some embodiments, data storage also includes storage and management for multiple subjects, for example, to make comparative analysis and/or improve artificial intelligence capabilities of the system.

In some embodiments, the protocol component comprises diagnostic protocols. In some embodiments, diagnostic protocols assess a subject's swallowing, breathing, speech, or other physical capability, for example, by assessing the amount of pressure a subject applies to one or more sensors of the intraoral component. For example, in one embodiment, the protocol instructs a processor to display a graphical image of the sensors of an intraoral component on a computer tablet. An individual sensor is highlighted on the display. The subject actuates the corresponding sensor with their tongue. If the subject depresses the incorrect sensor, a notice is provided on the display until the correct sensor is actuated. Once the correct sensor is actuated, the sensor reports the amount of pressure applied to the information processing component. The data is recorded. In some embodiments, the protocol instructs the processor to report the result to the subject or a healthcare provider, secure server, or other device. The process is repeated one or more times with one or more sensors. In some embodiments, the collected data represents the swallowing capability of the subject. In some embodiments, the collected data represents the breathing capability of the subject. The data may be compared to previous measurements to determine whether the subject has improved, maintained, or decreased capability. In some embodiments, the diagnostic protocol is used to assess the impact of a medical intervention (e.g., drug, surgery, diet change, etc.), adverse medical event (e.g., nerve damage, allergy, food interaction, poisoning, stroke, infection, cancer, etc.), or other event or process (e.g., aging) on swallowing capability.

In some embodiments, a diagnostic protocol comprising the steps of: 1) custom-molded mouthpiece is fitted to the patient; 2) maximum lingual isometric and/or pressures during swallowing are measured at 1 or more sensors. Repeat maximum values are collected to assure the maximum is representative of how the patient can typically perform. Once three values are collected that vary by less than 5%, the maximum value of those three presses is called the One repetition Maximum (1RM). If no three values vary by less than 5%, then the median value of nine maximum press attempts is considered the 1RM; 3) 1RM results are compared with age/gender normative data; 4) Therapeutic and/or further diagnostic recommendations are made based on results; 5) Repeat steps 2 and 3 to assess change over time.

In some embodiments, the protocol component comprises therapeutic protocols. In some embodiments, therapeutic protocols instruct a subject to use the intraoral device over a period of time to improve swallowing capability (e.g., increase swallowing capability, maintain swallowing capability, reduce the rate of loss of swallowing capability, etc.). In some such embodiments, an exercise regime is displayed to the subject. The exercise regime instructs the subject to actuate one or more of the pressure sensors with their tongue in a particular order, time, and/or amount of pressure. The specific protocol selected for the subject may be based on an initial screening or diagnostic test. Over time, alternative protocols are selected to continuously challenge the subject based on their current level of capability. Alternative intraoral components may be selected based on the level of skill of the subject. In some embodiments, data collected during the therapeutic protocol is used by a healthcare provider to optimize patient care and/or to diagnose medical conditions. For example, in some embodiments, the subject's performance over time (e.g., days, weeks, months, years), is monitored and aberrant results are flagged for further analysis. For example, if a subject is making steady improvement in swallowing strength, but then regresses, the cause of the regress is investigated or, based on the nature of the regress, perhaps diagnosed directly from the data.

The protocols employed can be selected and optimized for any desired improved function. In some embodiments, improved swallowing coordination (e.g., timing) is desired. In some embodiments, improved strength (e.g., pressure) is desired. In some embodiments, improved tongue base retraction is desired. In some embodiments, one or more of these improved functions, or other function, are desired. Improvement of such functions provides improved swallowing function, including but not limited to shorter bolus transit times and better bolus clearance.

In some embodiments, an exemplary 8-week course of treatment comprises:

Session 1—week 1 fit custom-molded mouthpiece; determine baseline maximum tongue pressures on 1 or more sensors and identify therapeutic goals. Therapy target is set at 60% of maximum. Patient completes 10 lingual press repetitions on each targeted sensor, 3 times per day on 3 days per week Session 2—week 2 increase therapeutic goals to 80% of baseline maximum. Patient completes 10 lingual press repetitions on each targeted sensor with new goals, 3 times per day on 3 days per week.

Session 3—week 3 remeasure maximum lingual pressures at 1 or more sensors and adjust therapy goals to 80% of new maximum values. Patient completes 10 lingual press repetitions on each targeted sensor with new goals, 3 times per day on 3 days per week.

Session 4—week 5 remeasure maximum pressures at 1 or more sensors adjust therapy goals to 80% of new maximum values. Patient completes 10 lingual press repetitions on each targeted sensor with new goals, 3 times per day on 3 days per week.

Session 5—week 7 remeasure maximum pressures at 1 or more sensors adjust therapy goals to 80% of new maximum values. Patient completes 10 lingual press repetitions on each targeted sensor with new goals, 3 times per day on 3 days per week. Session 6—week 8 remeasure maximum pressures at 1 or more sensors. Initiate maintenance program. Maintenance is 10 lingual press repetitions on each targeted sensor with goals from the final week of intensive therapy, 3 times per day on one day per week.

Protocol may be adjusted in duration and intensity and frequency according to patient's performance.

In some embodiments, the protocol component comprises alarms to maximize the likelihood that the system is used optimally. For example, in some embodiments, the protocol component comprises system diagnostics and any identified anomaly is noted with an alarm. Alarms include audio, text, graphical or other desired warnings sent to the subject, a medical caregiver, and/or system manufacturer/distributor. In some embodiments, alarms are used to ensure proper compliance with diagnostic or therapeutic protocols. For example, if the subject is not properly following the protocol, the display may indicate such and recommend the correct next step. Likewise, if the subject is using the system away from a healthcare provider (e.g., at home), and fails to follow a protocol (e.g., fails to keep up with a therapeutic protocol), a healthcare provider is provided with an alarm so that the subject can be contacted (e.g., by phone, text, e-mail, home visit, etc.) to ensure that the subject stays compliant with the protocol or to identify whether the patient is suffering from a medical condition or other circumstance that requires alteration of the protocol or urgent attention. In some embodiments, subjects are notified when software updates are available or then it is time for a therapy session.

In some embodiments, the protocol component comprises a calibration procedure. In some embodiments, the calibration procedure runs prior to conducting a therapeutic protocol to establish or confirm device operating parameters, establish "zero" levels, or otherwise prepare the device or subject for the therapeutic protocol(s).

In some embodiments, the protocol component has separate menus and features for different users of the system, such as subject and caregivers. For example, caregivers may be provided access to various aspects of a subject's therapy, including but not limited to: patient account creations, device commissioning, patient therapy routine records, graphs of therapy history, alerts for patients who are missing therapy or are digressing, protocol creation and publishing wizard, swallow administrative features, clinician authentication and credential management, historical record archiving, patient/patient family access to CMMS, patient/clinician messaging, FAQs for usage help, and help notification system.

The protocol component is built on any desired hardware/software platform. For example, in some embodiments, the system employs Microsoft's Azure environment to host the CMMS with Microsoft's .Net technology stack. C# is used as the development language, SQL Server for data storage and IIS as a web server.

In some embodiments, everything other than the caregiver's features and functions are contained in an at-home system. In such embodiments, the subject has the intraoral component, the communication component, the signal processing component, and the protocol component at their home and the caregiver accesses the needed features, functions, and alarms via an online interface. In some embodiments, a portion of the signal processing component and/or protocol component is maintained offsite. For example, in some embodiments, data is stored, sent, and received via a CMMS portal to the offsite location. This allows caregivers to view patient progress or respond to patient therapy issues from the CMMS. This also allows the system to function offline and resynchronize later when a connection is available. This also allows the system to send and receive updates on a regular basis, with a single update on the offsite server being able to service many systems at diverse locations.

In some embodiments, software components are provided via an application service provider (ASP) (e.g., are accessed by users within a web-based platform via a web browser across the Internet; is bundled into a network-type appliance and run within an institution or an intranet; or is provided as a software package and used as a stand-alone system on a single computer).

V) Chronic Disease Management Systems and Methods

In some embodiments, the systems and methods comprise chronic disease management (CDM) systems and methods. In some embodiments, the CDM system is an organization of patients, clinicians, and third-parties that exchange information with each other to effectuate management of chronic diseases.

In some embodiments, the CDM system comprises a patient device (e.g., any of the devices or systems described above) in contact and/or communication with a patient, a secure server, and a clinician device in contact and/or communication with a clinician. In some embodiments, the patient device generates a time-stamped metric based on the interaction between the patient and the patient device and relays that time-stamped metric to the secure server. In some embodiments, a secure server executes a protocol on a time-stamped metric to generate alerts (e.g., messages indicating that a certain metric level criteria has or has not been met) and/or reports (e.g., tables of metric values with or without time stamps) and relays those alerts and/or reports to a clinician device. In some embodiments, a clinician evaluates alerts and/or reports, makes a treatment decision, and communicates part or all of the treatment decision with a clinician device. In some embodiments, a clinician device relays messages and/or adjustments to a treatment plan to a secure server. In some embodiments, a secure server relays messages and/or adjustments to a patient device.

In some embodiments, the CDM system is used with the intraoral component, described herein, serving as part or all of the patient device and relaying information regarding lingual strength and exercise records in order to treat diseases such as dysphagia and sleep apnea. In some embodiments, the patient device measures blood pressure for treatment of hypertension, blood sugar for treatment of diabetes, peak expiratory flow for treatment of asthma or chronic obstructive pulmonary disorder, or weight for treatment of congestive heart failure.

In some embodiments, the CDM system allows a clinician to maintain persistent control over the treatment of a patient regardless of the patient's physical location. In some embodiments, a clinician remains in contact with a patient through the CDM system even as the patient moves among various settings (e.g., general hospitals, specialty care hospitals, nursing homes, long-term care facilities, ambulatory care centers, surgical centers, outpatient clinics, physicians' offices, rehabilitation centers, hospice centers, and the patient's home).

In some embodiments, provided herein are systems and methods for chronic disease management comprising of one or more or all of: a health monitoring device in contact and/or communication with a subject with a protocol; a secure server; and a clinician device in contact with a clinician. In some embodiments, the health monitoring device is configured to send time-stamped metrics and receive, collect, manage, and/or store messages from the secure server, the secure server is configured to receive, collect, manage, and/or store time-stamped metrics from the health monitoring device and messages from the clinician device, the secure server is configured to send messages to the health monitoring device and alerts and/or reports to the clinician device, and the clinician device is configured to send messages to and receive, collect, manage, and/or store alerts and/or reports from the secure server. In some embodiments, the health monitoring device is the intraoral component described herein.

In some embodiments, the chronic disease management systems and methods comprise a health monitoring device that receives information regarding lingual strength and frequency of lingual exercises from a patient. In some embodiments, this information is used to treat or manage swallowing disorders, sleep apnea, speech pathologies, etc.

In some embodiments, the methods for chronic disease management comprise one or more or all of the following: a subject performs an exercise, metrics about the exercise are reported to a health monitoring device; a subject performs an exercise using a health monitoring device; the health monitoring device sends a report comprising exercise metrics to a secure server; the secure server receives, collects, manages, and/or stores metrics regarding the exercise from the health monitoring device; the secure server sends alerts and/or reports based on the metrics to a clinician device; the clinician device receives, collects, manages, and/or stores alerts and/or reports from the secure server regarding the exercise; the clinician device sends messages informed by the alerts and/or reports to the health monitoring device directly or indirectly via the secure server; and a protocol of the health monitoring device is modified by the messages from the clinician. In some embodiments, the metrics are time-stamped.

In some embodiments, the systems and methods for chronic disease management are used to treat a swallowing disorder. In some embodiments, a subject with a swallowing disorder performs lingual exercises with an intraoral device. In some embodiments, the intraoral device relays metrics regarding the exercise to a clinician device directly or indirectly using one or more third parties. In some embodiments, a clinician receives the exercise metrics and devises treatment plan (e.g., the subject should perform more exercises, the subject should increase the intensity of the exercises, the subject should have the intraoral device refitted, the subject should obtain a new intraoral device, the subject should proceed without modification of the treatment plan, etc.). In some embodiments, the clinician uses the clinician device to send the treatment plan or other messages to the subject's intraoral device directly or via one or more third parties. In some embodiments, the intraoral device prompts the subject to perform the treatment plan sent by the clinician. In some embodiments, this CDM method is performed continuously independent of the patient's location.

In some embodiments, the clinician is able to access targets, settings, data logs, and any report or archived data. In some embodiments, clinicians have the ability to set certain parameters that users (e.g., patients) cannot access or easily access. In some such embodiments, control software is provided by a third party service provider and permissions for users and/or clinicians are set by the third party to a single user interface used by patients and clinicians (but having different access based on set permissions). In some embodiments, clinicians are able to override exercise target values by entering new values, determine which sensors are active, and determine the duration of the press repetition necessary to be within 10% of the target pressure. In some embodiments, the clinician is given access to various aspects of the patient's therapy including: patient account creation; device commissioning; patient therapy routine records; graphs of therapy history; alerts for patients who are missing therapy or are digressing; and protocol creation and publishing.

Figure 5:
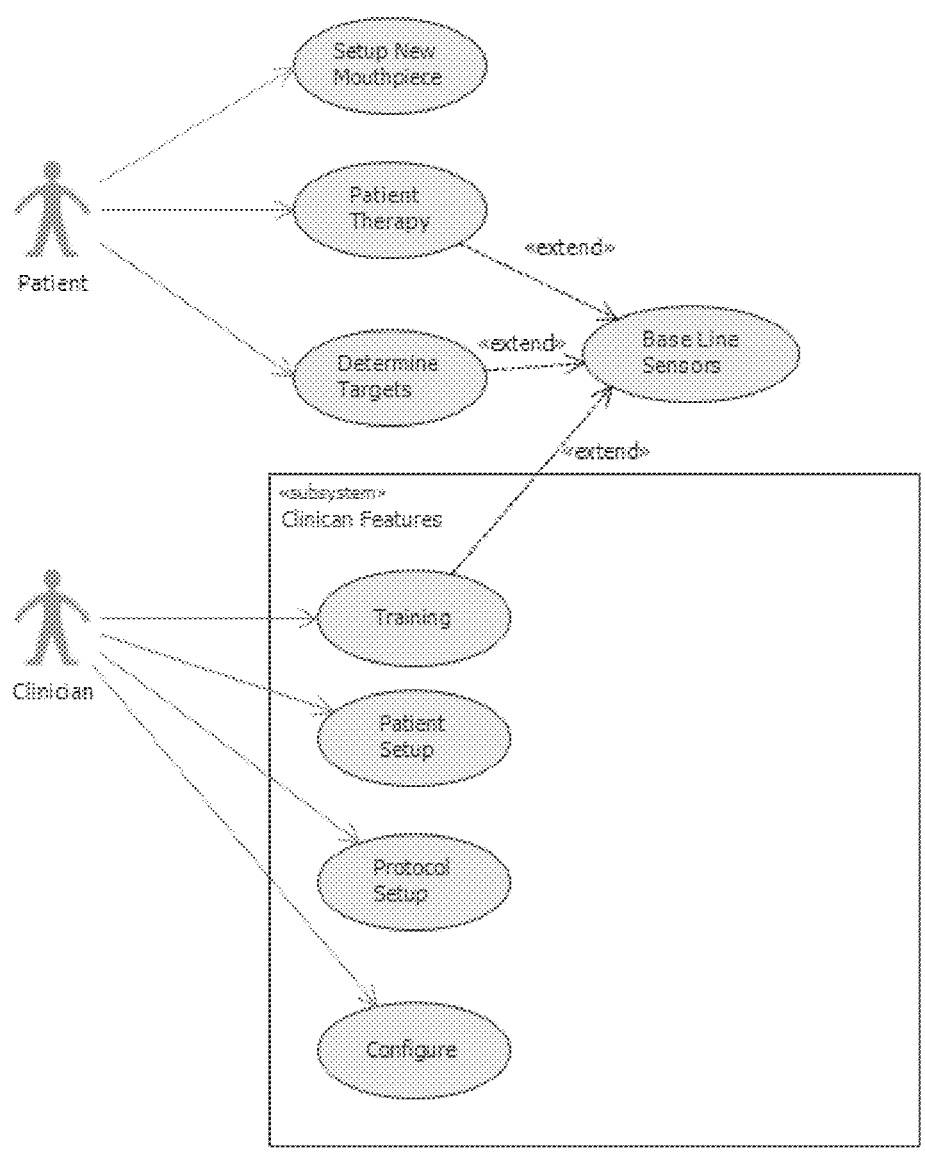
FIG. 5 shows an embodiment of a control system for managing devices and information between patients and clinicians.

An exemplary information control system is shown in FIG. 5. The patient accesses a web-based control software system and has access to several modules, including Setup New Mouthpiece (e.g., to register and initiate data collection for a new intraoral device); Patient Therapy (e.g., to select or manage protocols); Determine Targets (e.g., to set goals); and Base Line Sensors (e.g., to set baseline parameters of intraoral device sensors). The clinician accesses the web-based control software system and has access to several modules, including Training (e.g., to display mouthpiece; to display goal met counters; to display pressure readings; to configure saved and loads for all therapy sessions); Patient Setup (e.g., to initiate an account for a patient); Protocol Setup (e.g., to select or create a protocol for the patient; setting mandatory rest periods; press duration; target duration; repetition count; percent pressure variation tolerated for goal); and Configure (e.g., to configure system parameters such as associating the patient or clinician information with one or more facilities (e.g., hospitals; payers; etc.)).

Figure 6:
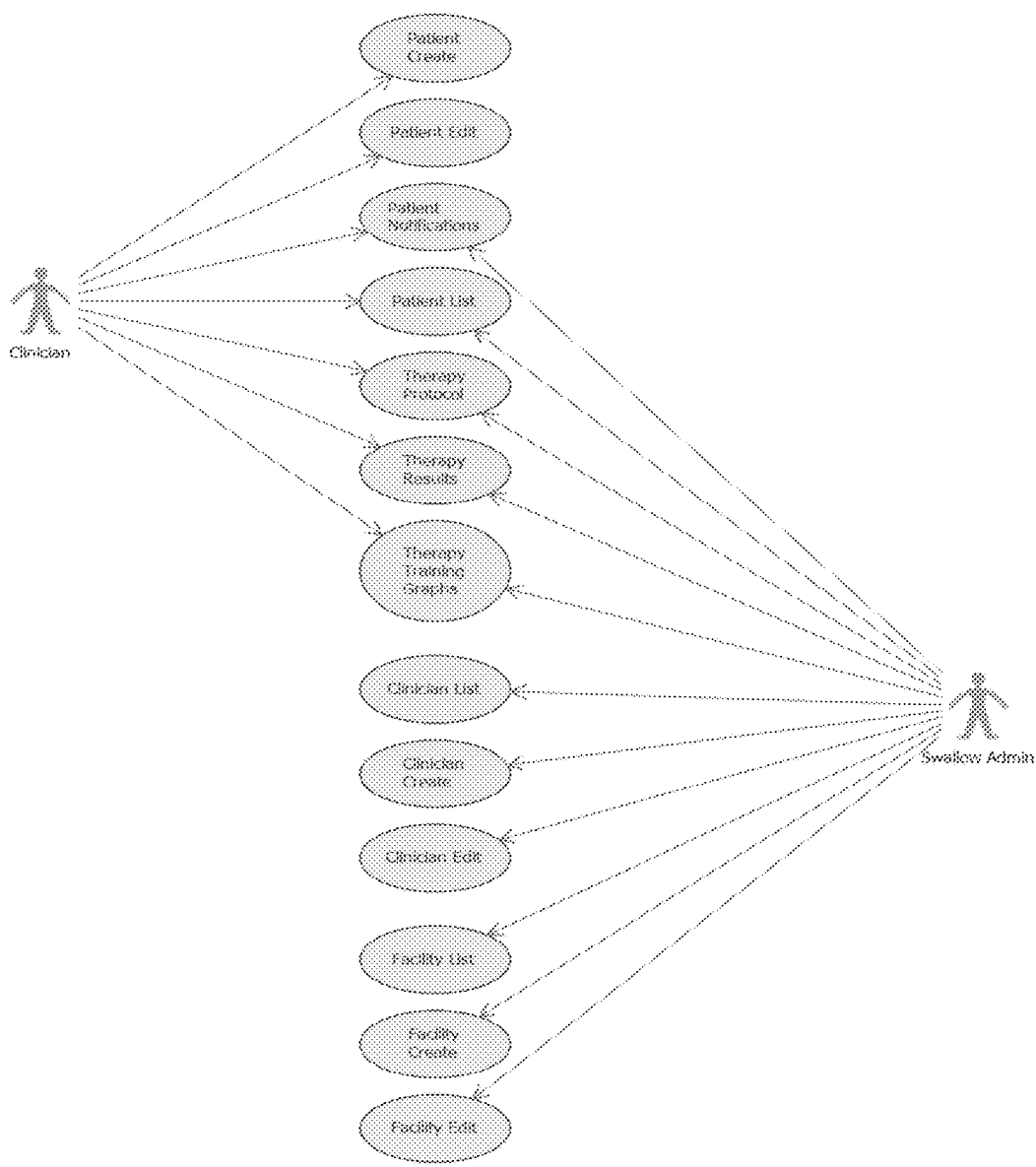
FIG. 6 shows an embodiment of a control system for managing devices and information between clinicians and service administrators.

FIG. 6 shows an exemplary control system as managed between a clinician and an administrator (e.g., third party service provided; hospital administrator, etc.). The clinician accesses a web-based control software system and has access to several modules, including Patient Create (e.g., to initiate an account for a patient); Patient Edit (e.g., to edit patient information); Patient Notifications (e.g., to set notifications for a particular patient or group of patients); Patient List (e.g., to manage multiple patients); Therapy Protocol (e.g., to create or select protocols); Therapy Results (e.g., to record and manage data from therapy); Therapy Training Graphs (e.g., to store and display data in graphical form). The administrator accesses the web-based control software system and has access to several modules, including the Patient Notification, Patient List, Therapy Protocol; Therapy Results; and Therapy Training Graphs of the clinician, as well as admin-only modules: Clinician List (e.g., to manage multiple clinicians); Clinician Create (e.g., to initiate an account for a clinician); Clinician Edit (e.g., to edit clinician information); Facility List (e.g., to manage multiple facilities, which may be associated with one or more clinicians); Facility Create (e.g., to initiate an account for a facility); and Facility Edit (e.g., to edit facility information). In some embodiments, the facility management component allows a single clinician to be associated with multiple different facilities or multiple clinicians at different facilities to be associated with a single patient account. Such embodiments allow fluid management of patient care for a subject or clinician that interacts with more than one caregiver or facility (e.g., as a subject transitions from a short term care facility to a long term care facility or home rehabilitation or vice versa).

In some embodiments, kits are provided comprising one or more or all of the components necessary, sufficient, or useful to practice any of the methods herein or assemble the systems herein. In some embodiments, a kit comprises one or more of: an intraoral device (or multiple thereof; e.g., 5-pack, 10-pack, 25-pack, etc.); a computing device or software (e.g., tablet computer; e.g., GOOGLE NEXUS 10); USB cable; circuit box; carrying case; and software (e.g., on a computer readable medium).

In some embodiments, the kit is packaged in a shipping container. For shipment and storage, in some embodiments, an intraoral device is placed in a resealable poly pouch and is contained within a small cell air encapsulated poly envelope. Sensor adapters and cords are placed within a poly pouch. The computing device (e.g., tablet) is placed in its own paperboard product carton and is wrapped in a graphics display sleeve. Beneath the tablet are paperboard compartments containing a charging cable and power adapter. A travel bag is placed on the bottom of a shipping containing.

In some embodiments, quality control and/or quality assurance systems and methods are provide to test and/or confirm the operation of one or more components of the systems and methods prior to use or in use. In some embodiments, one or more parameters is assessed. Such tests or parameters include, but are not limited to: clinician ability to specify which sensors are active for each user (e.g., for a multi-sensor intraoral device); measurement of pressures generated by the user preceded by a baseline measure to identify zero; multiple maximum pressures are collected to determine variability and the one repetition maximum (1RM) (pressure data can be collected at 100 Hz for maximum measurement); user feedback received after each repetition indicating whether a goal was met (e.g., defined as holding pressure against the sensor +/−10% of the pressure target, for a specific number of seconds within a four second window); data storage conducted and includes the number of repetitions completed and number of repetitions completed successfully meeting a goal; data stored is date and time stamped; data is in a format or formatted such that it is readable in a desired software system (e.g., MICROSOFT OFFICE SUITE); and data on target pressures, repetition completions, and success of repetitions is made available in text form.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A system for assessing swallowing function, comprising: a) an intraoral device comprising an adjustably bendable metal frame configured to be placed in a subject's mouth, said device, when placed in the subject's mouth having a central linear portion comprising a proximal end positioned towards an anterior opening of a mouth and a distal end positioned towards a back of the mouth; a first pressure sensor positioned on a first region of said frame; and a second pressure sensor positioned on a second region of said central linear portion of said frame near said distal end of said central linear portion, wherein said second region of said central linear portion of said frame positions said second pressure sensor at a boundary between a subject's hard and soft palate when said intraoral device is placed into a subject's mouth; and b) a computing device comprising a display and comprising a processor in electronic communication with said pressure sensors wherein said processor displays a diagnostic and therapeutic protocol to said subject that instructs said subject to actuate said pressure sensors with the subject's tongue over a period of time to improve lingual strength, wherein said protocol comprises: i) determining baseline maximum tongue pressure on said first or second pressure sensor; ii) selecting a therapeutic goal; iii) during a first time period, directing a plurality of tongue press repetitions of said first and second sensors at a pressure that is a percentage of said baseline maximum tongue pressure; iv) during a later second time period, directing a plurality of tongue press repetitions of said first and second sensors at a pressure that is an increased percentage of said baseline maximum tongue pressure; v) during a later third time period, re-measuring maximum lingual pressures at said first and second sensors and selecting a new therapeutic goal that is a percentage based the re-measured maximum lingual pressures; and vi) directing a plurality of tongue press repetitions of said first and second sensors based on said new therapeutic goal; and vii) repeating steps v) and vi) one or more times.

2. The system of claim 1, wherein said frame is stainless steel.

3. The system of claim 1, wherein said pressure sensors are located on an upper or lower surface of said frame.

4. The system of claim 1, wherein said pressure sensors comprise solid state pressure sensors.

5. The system claim 1, wherein said pressure sensors are polymer thick film (PTF) sensors that exhibit a decrease in resistance with increase in force applied to the surface of the sensor.

6. The system claim 1, wherein the computing device comprises a computer chip with a unique serial number.

7. The system of claim 1, wherein said frame has a composition and shape that provides tensile strength, malleability, and ductability sufficient to withstand stress associated with bending up to 90 degrees.

8. The system of claim 1, wherein said device further comprises a communication component that transmits information from said pressure sensors to said computing device.

9. The system of claim 8, wherein said communication component is a wireless communication component.

10. The system of claim 1, wherein said computing device comprises a tablet computer.

11. The system of claim 1, wherein said diagnostic and therapeutic protocol involves said computing device assessing sensor press direction, rest periods between sensor presses, target duration, and repetition count.

12. A method of assessing swallowing function, comprising:
    a) placing the intraoral device of the system of claim 1 within a mouth of a subject;
    b) bending said frame to position said sensors against a roof of said mouth;
    c) running said protocol comprising: i) determining baseline maximum tongue pressure on said first or second pressure sensor; ii) selecting a therapeutic goal; iii) during a first time period, directing a plurality of tongue press repetitions of said first and second sensors at a pressure that is a percentage of said baseline maximum tongue pressure; iv) during a later second time period, directing a plurality of tongue press repetitions of said first and second sensors at a pressure that is an increased percentage of said baseline maximum tongue pressure; v) during a later third time period, re-measuring maximum lingual pressures at said first and second sensors and selecting a new therapeutic goal that is a percentage based the re-measured maximum lingual pressures; and vi) directing a plurality of tongue press repetitions of said first and second sensors based on said new therapeutic goal; and vii) repeating steps v) and vi) one or more times.

13. The method of claim 12, wherein the subject performs the therapeutic protocol with said device, the device generates and sends metrics relating to the therapeutic protocol to a secure server, the secure server generates and sends alerts and/or reports relating to the therapeutic protocol to a clinician device, the clinician device sends messages informed by the alerts and/or reports to the device directly or indirectly via the secure server, and a protocol of the device is modified by the messages from the clinician device.

14. The method of claim 13, wherein said assessing and therapeutic regime comprises the steps of:
   a) in a first week, fitting said intraoral device to a mouth of a subject and determining baseline maximum tongue pressures on 1 or more sensors and identifying a therapeutic goal; completing 10 lingual press repetitions on each sensor, 3 times per day on 3 days in said first week at 60% of therapeutic goal;
   b) in a second week, completing 10 lingual press repetitions on each targeted sensor with an increased baseline maximum 3 times per day on 3 days per said second week;
   c) in a third week, re-measure maximum lingual pressures at 1 or more sensors and adjust therapy goals to 80% of new maximum values; completing 10 lingual press repetitions on each targeted sensor with the new goals, 3 times per day on 3 days per said third week; and
   d) repeat step c one or more times.

* * * * *